United States Patent [19]

Sugiyama et al.

[11] Patent Number: 4,596,801
[45] Date of Patent: Jun. 24, 1986

[54] 4H-3,1-BENZOXAZINE DERIVATIVES, PROCESS FOR PRODUCING THE SAME AND AGRICULTURAL OR HORTICULTURAL FUNGICIDE CONTAINING THE SAME

[75] Inventors: Hiroshi Sugiyama, Tokyo; Keizo Hosoda, Shizuoka; Yoshikazu Kumagai, Tokyo; Masaki Takeuchi; Masanori Okada, both of Saitama, all of Japan

[73] Assignee: Chugai Seiyaku Kabushiki Kaisha, Tokyo, Japan

[21] Appl. No.: 589,018

[22] Filed: Mar. 13, 1984

[30] Foreign Application Priority Data

Mar. 24, 1983 [JP] Japan .................................. 58-47967
Jan. 20, 1984 [JP] Japan .................................. 59-9331

[51] Int. Cl.$^4$ ................. C07D 265/14; C07D 265/22; C07D 265/20; A01N 43/86
[52] U.S. Cl. ............................ 514/227; 544/90; 544/92; 514/232; 514/239
[58] Field of Search ............... 544/90, 92; 424/248.4, 424/248.52, 248.57; 514/239, 240, 227, 232, 238

[56] References Cited

U.S. PATENT DOCUMENTS

| Re. 29,556 | 2/1978 | Adelstein | 544/124 |
|---|---|---|---|
| 3,634,455 | 1/1972 | Lednicer | 424/274 X |
| 3,725,404 | 4/1973 | Kuch et al. | 544/90 |
| 3,928,361 | 12/1975 | Baldwin et al. | 544/124 |
| 4,214,889 | 6/1980 | Myers et al. | 544/90 |
| 4,447,427 | 5/1984 | Klayman et al. | 544/124 |

OTHER PUBLICATIONS

March, *Advanced Organic Chemistry;* Reactions, Mechanisms & Structure, McGraw-Hill Co. (NY) 1968 pp. 38-39, 661-665.
Tachikawa, R. et al.: CA97:72307f; Studies on 1,3 Benzoxazines (1982).
Eiden, F. et al. CA81:3861q (1974) Acyl Enamines 26 Prep. and Reactions.
Huber-Emden; CA74:22856 (1971) 3-Acyl-3,4 Dihydro-2H-1,3-Benzoxazines Against Plant Fungi.
Chemical Abstracts, vol. 76, No. 19, May 8, 1972 #113064u, Lednicer et al., 2,3-Disubstituted 3H-Indol-3-Ols.
Patrick et al.–Journal of Organic Chem, vol. 19, No. 2 (1954), pp. 1824-1829.
Lednicer et al.; Journal of Heterocyclic Chemistry, vol VII (1970) pp. 575-581, "3H-Indol-3-Ols by a Novel Ring Contraction".

*Primary Examiner*—Glennon H. Hollrah
*Assistant Examiner*—Dara Dinner
*Attorney, Agent, or Firm*—Browdy and Neimark

[57] ABSTRACT

Novel 4H-3,1-benzoxazine derivative of the formula:

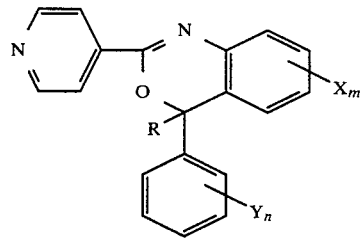

wherein X and Y each independently represent a halogen atom of a lower alkyl group; m and n each independently represent an integer of 0 to 2, and when m or n is 2, the plurality or each of X or Y may have the same or different meanings; R is a hydrogen atom, an alkyloxy group, an alkynyloxy group, an alkylthio group or an alkenylthio group, and a process for their production are provided. The compounds are highly effective against pathogenic fungi while being well tolerated by cultivated plants.

19 Claims, No Drawings

4H-3,1-BENZOXAZINE DERIVATIVES, PROCESS FOR PRODUCING THE SAME AND AGRICULTURAL OR HORTICULTURAL FUNGICIDE CONTAINING THE SAME

BACKGROUND OF THE INVENTION

1. Field of the Invention

The present invention relates to novel 4H-3,1-benzoxazine derivatives, a process for producing the same and an agricultural or horticultural fungicide containing the same.

2. Description of the Prior Art

Many synthetic organic compounds and antibiotics have been found to have the ability to kill fungi and several of them have been commercialized for use as agricultural and horticultural fungicides. However, these compounds are not completely safe since they often inhibit the growth of plants or are accompanied by herbicidal effects.

The present invention is the result of our extensive studies to develop a compound that has a novel basic structure and exhibits high efficacy even if it is used in a small amount as an effective ingredient.

SUMMARY OF THE INVENTION

One object of the present invention is to provide a novel 4H-3,1-Benzoxazine derivative which is highly effective against pathogenic fungi while having little toxic effect on cultivated plants, and a process for producing said compound.

Another object of the present invention is to provide a method for controlling pathogenic fungi on plants or in soil by use of said compound.

Further objects will become clear from the following descriptions.

DETAILED DESCRIPTION OF THE INVENTION

The novel 4H-3,1-Benzoxazine derivative of the invention is represented by formula (I):

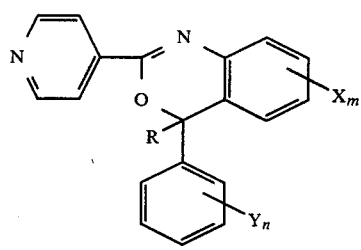

(I)

wherein X and Y each independently represent a halogen atom i.e. F, Cl, Br, I, or a lower alkyl group which may be straight or branched and having 1 to 4, preferably 1 to 2 carbon atoms; m and n each independently represent an integer of 0 to 2, and when m or n is 2, the plurality of each of X or Y may have the same or different meanings; R is a hydrogen atom, an alkyloxy group, an alkynyloxy group, an alkylthio group or an alkenylthio group.

When R has a meaning other than hydrogen, the alkyl, alkenyl or alkynyl moiety of said R may be straight or branched and it has 1 to 5 carbon atoms.

Preferred alkyloxy groups for R have 1 to 5 carbon atoms and more preferably they have 1 to 4 carbon atoms.

Preferred alkynyloxy groups for R have 3 to 4 carbon atoms and more preferably they have 2 to 3 carbon atoms.

Preferred alkylthio group for R have 1 to 4 carbon atoms and more preferably they have 1 to 3 carbon atoms.

Preferred alkenylthio groups for R have 3 to 4 carbon atoms and more preferably they have 2 to 3 carbon atoms.

The compound of formula (I) is novel and exhibits high efficacy against diseases affecting cultivated plants. However, this compound is by no means toxic to humans, animals or fish, and causes no adverse effects on cultivated plants.

The compound of formula (I) used in an agricultural fungicide has both preventive and curative effects against a wide spectrum of pathogenic fungi such as phycomycetes, Ascomycetes, Basidiomycetes and Deuteromycetes. The compound is particularly efficacious against powdery mildew, rust diseases, downy mildew and seedling damping-off which affect cultivated plants.

The compounds of formula (I) of the present invention may be produced by any of the following two methods. (1) The first method starts with a known benzophenone derivative of formula (II) (see, for example, Japanese Patent Laid Open Public No. 139306/80):

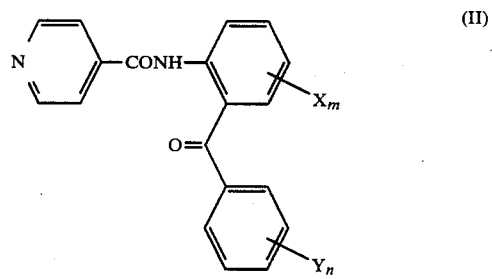

(II)

wherein X, Y, m and n have the same meanings as defined above. This starting material is reacted with a suitable halogenating agent such as thionyl chloride or thionyl bromide in the absence or presence of an inert solvent such as methylene chloride, chloroform, benzene or toluene. The resulting reaction product is then reacted with a corresponding alcohol (alcohols having branched chains are preferred for effecting a smooth reaction) or thiol to produce the desired compound of formula (I) wherein X, Y, m and n are the same as defined above; and R is an alkyloxy group, alkynyloxy group, an alkylthio group, or an alkenylthio group.

The reaction with alcohols or thiols can be carried out smoothly by using a suitable acid acceptor such as triethylamine, pyridine, sodium hydroxide, potassium hydroxide or sodium alkoxide.

The reaction in the first method is performed at a temperature of 0° to 90° C. for a period of 1 to 6 hours. (2) The second method starts with a benzhydrol derivative (III) that can be synthesized from the benzophenone derivative of formula (II) by a known method (see, for example, Japanese Patent Laid Open Public No. 59867/82):

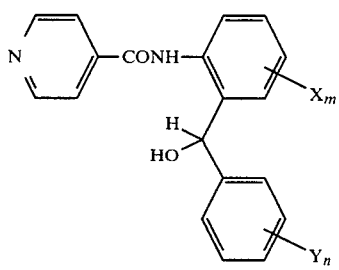

(III)

wherein X, Y, m and n are the same as defined above. The compound (III) is cyclized with a suitable halogenating agent (e.g. thionyl chloride, thionyl bromide or phosphorus trichloride), optionally in the presence of an inert solvent (e.g. benzene, toluene or chloroform) to obtain the desired compound of formula (I) wherein X, Y, m and n are the same as defined above; and R is a hydrogen atom.

The reaction in the second method may be satisfactorily performed at room temperature without any special heating or cooling operation. However, in general, the reaction is carried out in a temperature range of −5° to 30° C., preferably 0° to 20° C., for a period of 3 to 5 hours.

The production of compounds of formula (I) is illustrated by the following examples of synthesis.

SYNTHESIS 1

4-(4-Chlorophenyl)-4-isopropyloxy-2-(4-pyridyl)-4H-3,1-benzoxazine (Compound No. 27)

2-(4-Chlorobenzoyl)-isonicotinanilide (11.2 g) was added to thionyl chloride (100 ml) and the mixture was heated for 4 hours under reflux. Under reduced pressure, the thionyl chloride was distilled off completely. To the resulting reaction product, isopropyl alcohol (100 ml) was added, and triethylamine (15 ml) was slowly added dropwise with stirring under cooling with ice. After the completion of the addition, the mixture was stirred for another 2 hours at room temperature. Water was added to the reaction product and the mixture was extracted with ethyl acetate. The resulting ethyl acetate layer was dried over magnesium sulfate. After filtering off the magnesium sulfate, the ethyl acetate was distilled off under vacuum. Upon recrystallizing the residue from a mixed solvent of ethyl acetate and n-hexane, the titled compound was obtained in an amount of 10.1 g (yield: 80%). m.p. 114°–115° C.

Analysis: Calcd. for $C_{22}H_{19}ClN_2O_2$ (m.w. 378.85): C 69.75, H, 5.05, N 7.39 (%); Found: C 69.71, H 5.08, N 7.42 (%).

SYNTHESIS 2

4-(4-Chlorophenyl)-4-ethylthio-2-(4-pyridyl)-4H-3,1-benzoxazine (Compound No. 28)

The procedure of Synthesis 1 was repeated except that isopropyl alcohol was replaced by ethyl mercaptan (10 ml) in tetrahydrofuran (100 ml). The titled compound was obtained in an amount of 10.8 g (yield: 85%). m.p. 138°–139° C.

Analysis: Calcd. for $C_{21}H_{17}ClN_2OS$: (m.w. 380.88): C 66.22, H 4.50, N 7.35 (%); Found: C 66.14, H 4.48, N 7.39 (%).

SYNTHESIS 3

4-(4-Chlorophenyl)-2-(4-pyridyl)-4H-3,1-benzoxazine (Compound No. 4)

2-(4-Chloro-α-hydroxybenzyl)-isonicotinanilide (11.3 g) was added to pyridine (200 ml) under cooling with ice, and thionyl chloride (4 g) was then added slowly. The mixture was stirred for 1 hour. Following a continued stirring at room temperature, the reaction mixture was poured into water. The resulting crystal was separated by filtration and dissolved in ethyl acetate. After washing with water, the ethyl acetate solution was dried over anhydrous sodium sulfate. The anhydrous sodium sulfate was filtered off and the ethyl acetate was distilled off under vacuum. Upon recrystallizing the residue with a mixed solvent of ethyl acetate and n-hexane, the crystal of the compound was obtained in an amount of 9.8 g (yield: 92%).

m.p. 116°–117° C.

Analysis: Calcd. for $C_{19}H_{13}ClN_2O$ (m.w. 320.77): C 71.14, H 4.08, N 8.73; Found: C 71.19, H 4.01, N 8.70.

SYNTHESIS 4

4-(4-Chlorophenyl)-6-fluoro-2-(4-pyridyl)-4H-3,1-benzoxazine (Compound No. 11)

2-(4-Chloro-α-hydroxybenzyl)-4-fluoro-isonicotinanilide (11.9 g) was treated as in Synthesis 3. The titled compound was obtained in an amount of 10.2 g (yield: 90%).

m.p. 144°–145° C.

Analysis: Calcd. for $C_{19}H_{12}ClFN_2O$ (m.w. 338.77): C 67.36, H 3.57, N 8.27; Found: C 67.31, H 3.62, N 8.23.

SYNTHESIS 5

4-(4-Bromophenyl)-7-chloro-8-methyl-2-(4-pyridyl)-4H-3,1-benzoxazine (Compound No. 22)

2-(4-bromo-α-hydroxybenzyl)-5-chloro-6-methylisonicotinanilide (14.4 g) was treated as in Synthesis 3. The titled compound was obtained in an amount of 11.7 g (yield: 85%). m.p. 169°–170° C.

Analysis: Calcd. for $C_{20}H_{14}BrClN_2O$ (m.w. 413.69): C 58.07, H 3.41, N 6.77; Found: C 58.13, H 3.37, N 6.76.

SYNTHESIS 6

6-Chloro-4-(4-chlorophenyl)-2-(4-pyridyl)-4H-3,1-benzoxazine (Compound No. 8)

To chloroform (300 ml), 4-chloro-2-(4-chloro-α-hydroxybenzyl)-isonicotinanilide (12.4 g) and triethylamine (5.0 ml) were added. With stirring and under cooling with ice, phosphorus tribromide (9.1 g) was added slowly, and the stirring was continued for 1 hour. Following another 3-hour stirring at room temperature, the reaction mixture was poured into water. The chloroform layer was thoroughly washed with water and subsequently dried. The chloroform was completely distilled off under vacuum. Upon recrystallization from a mixed solvent of ethyl acetate and n-hexane, the titled compound was obtained in an amount of 10.1 g (yield: 85%). m.p. 140°–141° C.

Analysis: Calcd. for $C_{19}H_{12}Cl_2N_2O$ (m.w. 352.33): C 64.24, H 3.41, N 7.89; Found: C 64.29, H 3.38, N 7.91.

SYNTHESIS 7

6-Bromo-4-phenyl-2-(4-pyridyl)-4H-3,1-benzoxazine (Compound No. 3)

4-Bromo-2-(α-hydroxybenzyl)-isonicotinanilide (12.8 g) was treated as in Synthesis 6 except that triethylamine was replaced by diethylaniline (6.0 ml). The titled compound was obtained in an amount of 10.3 g (yield: 85%).

m.p. 161°–162° C.

Analysis: Calcd. for $C_{19}H_{13}BrN_2O$ (m.w. 365.22): C 62.49, H 3.59, N 7.67; Found: C 62.43, H 3.61, N 7.65.

Several other compounds of formula (I) were prepared in a like manner, and they are listed in Table 1 as non-limiting examples together with the compounds prepared by Syntheses Nos. 1 to 7.

The respective numbers used in Table 1 to indicate the positions of substituents X and Y have the following definitions:

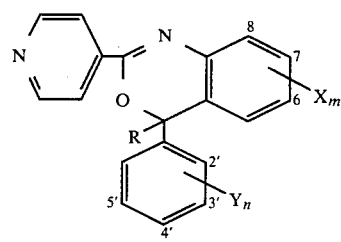

The identification numbers of the compounds listed in Table 1 shall apply to the experiments and preparation of fungicide formulations shown later in this specification.

TABLE 1

| Compound No. | X 6 | X 7 | X 8 | m | Y 2' | Y 3' | Y 4' | Y 5' | n | R | m.p. (°C.) |
|---|---|---|---|---|---|---|---|---|---|---|---|
| 1 | H | H | H | 0 | H | H | H | H | 0 | H | 108–109 |
| 2 | Cl | H | H | 1 | H | H | H | H | 0 | H | 153–154 |
| 3 | Br | H | H | 1 | H | H | H | H | 0 | H | 161–162 |
| 4 | H | H | H | 0 | H | H | Cl | H | 1 | H | 116–117 |
| 5 | H | H | H | 0 | F | H | H | H | 1 | H | 118–119 |
| 6 | Cl | H | H | 1 | Cl | H | H | H | 1 | H | 141–142 |
| 7 | Cl | H | H | 1 | H | Cl | H | H | 1 | H | 124–125 |
| 8 | Cl | H | H | 1 | H | H | Cl | H | 1 | H | 140–141 |
| 9 | Cl | H | H | 1 | H | H | F | H | 1 | H | 148–150 |
| 10 | Cl | H | H | 1 | H | H | Br | H | 1 | H | 140–141 |
| 11 | F | H | H | 1 | H | H | Cl | H | 1 | H | 144–145 |
| 12 | Br | H | H | 1 | H | H | Cl | H | 1 | H | 154–155 |
| 13 | H | H | H | 0 | Cl | H | Cl | H | 2 | H | 115–116 |
| 14 | Cl | H | H | 1 | H | Cl | Cl | H | 2 | H | 100–102 |
| 15 | CH$_3$ | H | H | 1 | H | H | H | H | 0 | H | 154–155 |
| 16 | H | H | H | 0 | H | H | Br | H | 1 | H | 124–125 |
| 17 | CH$_3$ | CH$_3$ | H | 2 | H | H | Cl | H | 1 | H | 168–170 |
| 18 | Cl | H | CH$_3$ | 2 | H | H | Cl | H | 1 | H | 126–127 |
| 19 | CH$_3$ | H | Cl | 2 | H | H | Cl | H | 1 | H | 152–153 |
| 20 | CH$_3$ | H | CH$_3$ | 2 | H | H | Cl | H | 1 | H | 117–118 |
| 21 | H | CH$_3$ | CH$_3$ | 2 | H | H | F | H | 1 | H | 89–90 |
| 22 | H | Cl | CH$_3$ | 2 | H | H | Br | H | 1 | H | 169–170 |
| 23 | CH$_3$ | H | H | 1 | H | H | Cl | H | 1 | —O.CH(CH$_3$)$_2$ | 143–144 |
| 24 | H | H | H | 0 | H | H | Cl | H | 1 | —O.CH$_2$C≡CH | 140–141 |
| 25 | H | H | H | 0 | H | H | Br | H | 1 | —S.CH$_3$ | NMR δ (CDCl$_3$) 2.0 (s, 3H) 7.5–8.7 (m, 12H) |
| 26 | Cl | H | H | 1 | H | H | Cl | H | 1 | —O.CH(CH$_3$)$_2$ | 160–161 |
| 27 | H | H | H | 0 | H | H | Cl | H | 1 | —O.CH(CH$_3$)$_2$ | 114–115 |
| 28 | H | H | H | 0 | H | H | Cl | H | 1 | —S.CH$_2$CH$_3$ | 138–139 |
| 29 | H | H | H | 0 | H | H | Br | H | 1 | —S.CH$_2$CH$_3$ | 126–127 |
| 30 | H | H | H | 0 | H | H | CH$_3$ | H | 1 | —S.CH$_2$CH$_3$ | 103–104 |
| 31 | H | H | H | 0 | H | H | Cl | H | 1 | —S.CH$_2$CH$_2$CH$_3$ | 126–127 |
| 32 | H | H | H | 0 | H | H | Br | H | 1 | —S.CH$_2$CH$_2$CH$_3$ | 118–119 |
| 33 | H | H | H | 0 | H | H | CH$_3$ | H | 1 | —S.CH$_2$CH$_2$CH$_3$ | 104–105 |

TABLE 1 -continued

| Compound No. | X | | | m | Y | | | | n | R | m.p. (°C.) |
|---|---|---|---|---|---|---|---|---|---|---|---|
| | 6 | 7 | 8 | | 2' | 3' | 4' | 5' | | | |
| 34 | H | H | H | 0 | H | H | Cl | H | 1 | —S.CH(CH₃)₂ | 134–135 |
| 35 | H | H | H | 0 | H | H | CH₃ | H | 1 | —S.CH(CH₃)₂ | 148–149 |
| 36 | Cl | H | H | 0 | H | H | H | H | 1 | —O.CH₃ | 98–99 |
| 37 | H | H | H | 0 | H | H | Cl | H | 1 | —S.CH₂CH=CH₂ | 122–123 |
| 38 | H | H | H | 0 | H | H | Cl | H | 1 | —O.CH(CH₃)(C₂H₅) | 118–119 |
| 39 | H | H | H | 0 | H | H | Cl | H | 1 | —O.CH₂CH₃ | 80–81 |

The compounds of the present invention thus prepared have systemic effects on plants, so they can be applied in various manners to treat the stem and foliage of plants over the ground, seeds, the surface of water, and the soil.

The compounds of the present invention have no adverse effects on the cultivated plants to be treated, so they can be used either before or after sowing or at any stage of the plant growth whether it is a juvenile seedling, in the midst of growth or in the fruiting stage.

The compounds of the present invention may be used alone without mixing with other ingredients. But in order to provide greater convenience, they may be mixed with various solid or liquid agricultural carriers so as to formulate wettable powders, emulsifiable concentrates, oils, dusts, granules or suspension concentrates. These formulations may be further supplemented with adjuvants such as dispersants, diluents, emulsifiers, spreaders, wetting agents, adsorbents, thickners, anti-foaming agents and anti-freezing agents. The solids and liquid carriers may be used either alone or in combination. Illustrative carriers include talc, clay, bentonite, kaolin, diatomaceous earth, calcium carbonate, wood-meal, starch, gum arabic, water, alcohol, kerosene, naphtha, xylene, cyclohexanone, methylnaphthalene, benzene, acetone, dimethylformamide, glycol ether and N-methylpyrrolidone.

Suitable adjuvants include polyoxyethylene alkylphenyl ether, polyoxyethylene sorbitan monooleate, ethylene oxide-propylene oxide copolymer, lignin sulfonate, sorbitan esters, soaps, sulfated oils, alkyl sulfate esters, petroleum sulfonates, dioctyl sulfo-succinates, alkylbenzenesulfonates, aliphatic amine salts, quaternary ammonium salts, alkyl pyridinium salts, alkylaminoethyl glycine, alkyldimethyl betaine, polyglycol sulfate esters, alkylamine sulfonic acid, isopropyl phosphate, carboxymethyl cellulose, polyvinyl alcohol, hydroxypropyl cellulose, ethylene glycol and xanthan gum.

The compounds of the present invention may also be mixed with propellants such as fluorotrichloromethane and dichlorodifluoromethane for use as aerosols. Alternatively, the compounds may be mixed with suitable foaming agents or combustion aids to prepare fumigants or formulations for smoking.

When preparing fungicides from the compounds of the present invention, they are generally used in an amount, on a weight basis, of 0.05 to 95%, preferably 0.1 to 80%, more preferably 1 to 70%, with the carriers and adjuvants being used in amounts of 70 to 99% and 0 to 20%, respectively. In order to achieve a wide spectrum of effects, the compounds may be used in combination with fertilizers or other fungicides or agrochemicals such as herbicides, plant growth regulators, insecticides and acaricides.

The concentrations of the compounds of the present invention and the relevant amounts to be applied will vary with many factors such as the season, weather, method of application, type of formulation, the location of use, the disease to be combatted and the crop plant to be treated. Generally, the concentrations of the compounds are in the range of 0.5 to 1,000 ppm, preferably 3 to 500 ppm. The amounts of the compounds applied generally range from 0.5 to 500 g, preferably from 1 to 250 g, for 10 ares.

The efficacy of the compounds of the present invention as agricultural and horticultural fungicides will become apparent by reading the following results of experiments.

EXPERIMENT 1

Test for Control on Powdery Mildew of Cucumber (Protective Effect)

A biscuit pot with a diameter of 15 cm was filled with horticultural granular soil, and ten seeds of Takasago strain cucumber were sown. After cultivation under greenhouse conditions for 10 days, the juvenile seedlings with cotyledon were tested.

These seedlings were sprayed with a dose of 15 ml per pot of a wettable powder of Formulation 2, described below which had been diluted with water at a predetermined concentration. After air drying, the seedlings were inoculated with a suspension of conidiospores of *Sphaerotheca fuliginea* by spraying it on the foliage of the seedlings. Then, the cultivation was effected at a temperature of from 23° to 26° C. for 10 days, and the seedlings were checked for the occurrence and severity of infection in terms of percent infection calculated as follows.

First, on the basis of the percentage of infected area, the test seedlings were rated on the following infection index of from 0 to 5.

| Infection index | Condition of the leaf |
|---|---|
| 0 | No infected area on leaf surface |
| 1 | Infected area of less than 10% on leaf surface |
| 2 | Infected area of less than 30% on leaf surface |
| 3 | Infected area of less than 60% on leaf surface |
| 4 | Infected area of less than 80% on leaf surface |
| 5 | Infected area not less than 80% on leaf surface |

Percent infection was calculated from the Infection indexes thus obtained according to the following equation:

$$\text{Percent infection} = \frac{\Sigma(\text{infection index} \times \text{number of leaves})}{5 \times (\text{total number of checked leaves})} \times 100.$$

Percent protection was obtained by comparing the percent infections (P.I.) of untreated seedlings and treated seedlings, according to the following equation:

$$\text{Percent protection} = \frac{(\text{P.I. of untreated seedlings}) - (\text{P.I. of treated seedlings})}{(\text{P.I. of untreated seedlings})} \times 100.$$

The results are shown in Table 2.

TABLE 2

| Compound No. | Concentration of the compound (ppm) | Percent infection | Percent protection | Toxicity |
|---|---|---|---|---|
| untreated section | — | 100 | — | — |
| 1 | 150 | 0 | 100 | non |
| 2 | 150 | 0 | 100 | non |
| 3 | 150 | 0 | 100 | non |
| 4 | 150 | 0 | 100 | non |
| 5 | 150 | 0 | 100 | non |
| 6 | 150 | 1.5 | 98.5 | non |
| 7 | 150 | 1 | 99 | non |
| 8 | 150 | 0 | 100 | non |
| 9 | 150 | 0 | 100 | non |
| 10 | 150 | 0 | 100 | non |
| 11 | 150 | 0 | 100 | non |
| 12 | 150 | 0 | 100 | non |
| 13 | 150 | 0 | 100 | non |
| 16 | 150 | 0 | 100 | non |
| 18 | 150 | 0 | 100 | non |
| 20 | 150 | 0 | 100 | non |
| 22 | 150 | 0 | 100 | non |
| 25 | 150 | 0 | 100 | non |
| 26 | 150 | 0 | 100 | non |
| 27 | 150 | 0 | 100 | non |
| 28 | 150 | 0 | 100 | non |
| 29 | 150 | 0 | 100 | non |
| 31 | 150 | 0 | 100 | non |
| 34 | 150 | 0 | 100 | non |
| 36 | 150 | 0 | 100 | non |

EXPERIMENT 2

Test for Control on Powdery Mildew of Cucumber (Curative Effect)

A biscuit pot with a diameter of 15 cm was filled with horticultural granular soil, and ten seeds of Takasago strain cucumber were sown. After cultivation under greenhouse conditions for 10 days, the juvenile seedlings with completely developed cotyledon were tested.

The seedlings were inoculated with a suspension of conidiospores of *Sphaerotheca fuliginea* by spraying, and after leaving at a temperature of from 23° to 26° C. for one day, were sprayed with a dose of 15 ml per pot of an emulsion prepared from Formulation 3, described below, by dilution with water at a predetermined concentration. After air drying, the seedlings were cultivated at 23°-26° C. under greenhouse conditions for 10 days, and checked for the occurrence and severity of infection.

Infection index, percent infection and percent protection on this experiment were determined as in Experiment 1.

The results are shown in Table 3 below.

TABLE 3

| Compound No. | Concentration of the compound (ppm) | Percent infection | Percent protection | Toxicity |
|---|---|---|---|---|
| untreated section | — | 100 | — | — |
| 1 | 150 | 0 | 100 | non |
| 2 | 150 | 0 | 100 | non |
| 3 | 150 | 0 | 100 | non |
| 4 | 150 | 0 | 100 | non |
| 5 | 150 | 0 | 100 | non |
| 6 | 150 | 5 | 95 | non |
| 7 | 150 | 0 | 100 | non |
| 8 | 150 | 0 | 100 | non |
| 9 | 150 | 0 | 100 | non |
| 10 | 150 | 0 | 100 | non |
| 11 | 150 | 0 | 100 | non |
| 12 | 150 | 0 | 100 | non |
| 13 | 150 | 0 | 100 | non |
| 14 | 150 | 10 | 90 | non |
| 16 | 150 | 0 | 100 | non |
| 17 | 150 | 0 | 100 | non |
| 18 | 150 | 0 | 100 | non |
| 20 | 150 | 0 | 100 | non |
| 21 | 150 | 0 | 100 | non |
| 22 | 150 | 0 | 100 | non |
| 25 | 150 | 0 | 100 | non |
| 26 | 150 | 0 | 100 | non |
| 27 | 150 | 0 | 100 | non |
| 28 | 150 | 0 | 100 | non |
| 29 | 150 | 0 | 100 | non |
| 36 | 150 | 0 | 100 | non |
| 37 | 150 | 0 | 100 | non |
| 38 | 150 | 0 | 100 | non |
| 39 | 150 | 0 | 100 | non |

EXPERIMENT 3

Test for Control on Powdery Mildew of Wheat (Protective Effect)

A biscuit pot with a diameter of 12 cm was filled with horticultural granular soil known by the name of "Arakida" and 15 grains of wheat (Norin No. 61 strain) were seeded. After cultivation under greenhouse conditions for 12 days, the juvenile seedlings at the one-leaf stage were subjected to the following test.

These seedlings were sprayed with a dose of 15 ml per pot of emulsifiable concentrate of Formulation 4, described below which had been diluted with water at a predetermined concentration. After air drying, the seedlings were inoculated with a suspension of conidiospores of *Erysiphe graminis*, and after cultivation at a temperature of from 20° to 24° C. under greenhouse conditions for 10 days, were checked for the occurrence and severity of infection.

Infection index, percent infection and percent protection were determined as in Experiment 1.

The results are shown in Table 4 below.

TABLE 4

| Compound No. | Concentration of the compound (ppm) | Percent infection | Percent protection | Toxicity |
| --- | --- | --- | --- | --- |
| untreated section | — | 100 | — | — |
| 1 | 150 | 0 | 100 | non |
| 2 | 150 | 0 | 100 | non |
| 3 | 150 | 0 | 100 | non |
| 4 | 150 | 0 | 100 | non |
| 5 | 150 | 0 | 100 | non |
| 8 | 150 | 0 | 100 | non |
| 9 | 150 | 0 | 100 | non |
| 10 | 150 | 0 | 100 | non |
| 11 | 150 | 0 | 100 | non |
| 12 | 150 | 0 | 100 | non |
| 13 | 150 | 0 | 100 | non |
| 14 | 150 | 0 | 100 | non |
| 16 | 150 | 0 | 100 | non |
| 17 | 150 | 0 | 100 | non |
| 18 | 150 | 0 | 100 | non |
| 20 | 150 | 0 | 100 | non |
| 22 | 150 | 0 | 100 | non |
| 24 | 150 | 0 | 100 | non |
| 25 | 150 | 0 | 100 | non |
| 26 | 150 | 0 | 100 | non |
| 27 | 150 | 0 | 100 | non |
| 28 | 150 | 0 | 100 | non |
| 29 | 150 | 0 | 100 | non |
| 31 | 150 | 0 | 100 | non |
| 32 | 150 | 0 | 100 | non |
| 34 | 150 | 0 | 100 | non |
| 36 | 150 | 0 | 100 | non |

EXPERIMENT 4

Test for Control of Powdery Mildew of Wheat (Curative Effect)

A biscuit pot with a diameter of 12 cm was filled with horticultural granular soil known by the name of "Arakida", and 15 grains of wheat (Norin No. 61 strain) were seeded. Then cultivation was effected under greenhouse conditions for 12 days and the juvenile seedlings at the one-leaf stage were used for the following tests.

These seedlings were inoculated by spraying with a suspension of conidiospores of *Erysiphe graminis,* and after allowing to stand for one day at 20°–23° C. under greenhouse conditions, were sprayed with a dose of 15 ml of wettable powder of Formulation 2, described below, which had been diluted with water at a predetermined concentration. After air drying, the seedlings were cultivated at 20°–24° C. under greenhouse conditions for 10 days and checked for the occurrence and severity of infection.

Infection index, percent infection and percent protection were determined as in Experiment 1.

The results are shown in Table 5 below.

TABLE 5

| Compound No. | Concentration of the compound (ppm) | Percent infection | Percent protection | Toxicity |
| --- | --- | --- | --- | --- |
| untreated section | — | 100 | — | — |
| 1 | 150 | 0 | 100 | non |
| 2 | 150 | 0 | 100 | non |
| 3 | 150 | 0 | 100 | non |
| 4 | 150 | 0 | 100 | non |
| 5 | 150 | 0 | 100 | non |
| 7 | 150 | 0 | 100 | non |
| 8 | 150 | 0 | 100 | non |
| 9 | 150 | 0 | 100 | non |
| 10 | 150 | 0 | 100 | non |
| 11 | 150 | 0 | 100 | non |
| 12 | 150 | 0 | 100 | non |
| 13 | 150 | 0 | 100 | non |
| 14 | 150 | 0 | 100 | non |
| 16 | 150 | 15 | 85 | non |
| 20 | 150 | 0 | 100 | non |
| 21 | 150 | 0 | 100 | non |
| 22 | 150 | 0 | 100 | non |
| 25 | 150 | 0 | 100 | non |
| 26 | 150 | 0 | 100 | non |
| 27 | 150 | 0 | 100 | non |
| 28 | 150 | 0 | 100 | non |
| 29 | 150 | 0 | 100 | non |
| 31 | 150 | 0 | 100 | non |
| 32 | 150 | 0 | 100 | non |
| 34 | 150 | 0 | 100 | non |
| 36 | 150 | 0 | 100 | non |

EXPERIMENT 5

Test for Control on Powdery Mildew of Cucumber (Protective Effect)

Test similar to those in Experiment 1 were conducted except for using a smaller dose of the active compound as shown.

The results are given in Table 6.

TABLE 6

| Compound No. | Concentration of the compound (ppm) | Percent infection | Percent protection | Toxicity |
| --- | --- | --- | --- | --- |
| untreated section | — | 100 | — | — |
| 4 | 100 | 0 | 100 | non |
|   | 6.2 | 0 | 100 | non |
| 8 | 100 | 0 | 100 | non |
|   | 6.2 | 0 | 100 | non |
| 10 | 100 | 0 | 100 | non |
|   | 6.2 | 0 | 100 | non |
| 16 | 100 | 0 | 100 | non |
|   | 6.2 | 0 | 100 | non |
| 20 | 100 | 0 | 100 | non |
|   | 6.2 | 0 | 100 | non |
| 22 | 100 | 0 | 100 | non |
|   | 6.2 | 0 | 100 | non |
| 26 | 100 | 0 | 100 | non |
|   | 6.2 | 0 | 100 | non |
| 27 | 100 | 0 | 100 | non |
|   | 6.2 | 0 | 100 | non |
| 28 | 100 | 0 | 100 | non |
|   | 6.2 | 0 | 100 | non |
| 29 | 100 | 0 | 100 | non |
|   | 6.2 | 0 | 100 | non |
| 31 | 100 | 0 | 100 | non |
|   | 6.2 | 0 | 100 | non |
| 36 | 100 | 0 | 100 | non |
|   | 6.2 | 0 | 100 | non |

EXPERIMENT 6

Test for Control on Powdery Mildew of Cucumber (Curative Effect)

Tests similar to those in Experiment 2 were conducted except for using a smaller dose of the active compound as indicated below.

The results are shown in Table 7.

TABLE 7

| Compound No. | Concentration of the compound (ppm) | Percent infection | Percent protection | Toxicity |
| --- | --- | --- | --- | --- |
| untreated section | — | 100 | 0 | — |
| 4 | 100 | 0 | 100 | non |
|  | 6.2 | 0 | 100 | non |
| 8 | 100 | 0 | 100 | non |
|  | 6.2 | 0 | 100 | non |
| 11 | 100 | 0 | 100 | non |
|  | 6.2 | 0 | 100 | non |
| 16 | 100 | 0 | 100 | non |
|  | 6.2 | 0 | 100 | non |
| 17 | 100 | 0 | 100 | non |
|  | 6.2 | 0 | 100 | non |
| 26 | 100 | 0 | 100 | non |
|  | 6.2 | 0 | 100 | non |
| 27 | 100 | 0 | 100 | non |
|  | 6.2 | 0 | 100 | non |
| 29 | 100 | 0 | 100 | non |
|  | 6.2 | 0 | 100 | non |
| 31 | 100 | 0 | 100 | non |
|  | 6.2 | 0 | 100 | non |

EXPERIMENT 7

Test for Control on Downy Mildew of Cucumber (Protective Effect)

A biscuit pot with a diameter of 12 cm was filled with commercial horticulture soil (Kureha Kagaku, Tokyo, Japan), seeds of cucumber (Ochiai-aonagafushinari strain) were sown and cultivated under greenhouse conditions for 10 days. The juvenile seedlings with cotyledon were sprayed with an emulsifiable concentrate of the compound which had been diluted with water at a predetermined concentration so that the surface of the leaves were fully wetted with the sprayed emulsion of Formulation 3. Then, the seedlings were cultivated under greenhouse conditions for two days, and inoculated with a suspension of conidiospores of *Pseudoperonospora cubensis* by spraying it as an aqueous suspension. The treated seedlings were allowed to stand at 21°–22° C. in a humid atmosphere for 3 days, cultivated at 21°–22° C. under the light of fluorescent lamps, and checked for the occurrence and severity of infection in terms of percent infection, calculated as follows.

First, on the basis of the percentage of infected area, the test seedlings were rated on the infection index of from 0 to 5.

| Infection index | Condition of the leaf |
| --- | --- |
| 0 | No infected area on leaf surface |
| 1 | Infected area of less than 5% on leaf surface |
| 2 | Infected area of less than 20% on leaf surface |
| 3 | Infected area of less than 50% on leaf surface |
| 4 | Infected area of less than 80% on leaf surface |
| 5 | Infected area not less than 80% on leaf surface |

Second, on the basis of the infection indexes, percent infection was calculated by the following equation:

$$\text{Percent infection} = \frac{\Sigma(\text{infection index} \times \text{number of leaves})}{(\text{total number of checked leaves}) \times 5} \times 100.$$

Then, percent protection was calculated on the basis of the equation below.

$$\text{Percent protection} = \frac{(\text{percent infection in untreated seedlings}) - (\text{percent infection in treated seedlings})}{(\text{percent infection in untreated seedlings})} \times 100.$$

The results are shown in Table 8.

TABLE 8

| Compound No. | Concentration of the compound (ppm) | Percent infection | Percent protection | Toxicity |
| --- | --- | --- | --- | --- |
| untreated section | — | 100 | — | — |
| 4 | 250 | 0 | 100 | non |
| 8 | 250 | 0 | 100 | non |
| 11 | 250 | 0 | 100 | non |
| 16 | 250 | 0 | 100 | non |
| 22 | 250 | 0 | 100 | non |
| 26 | 250 | 0 | 100 | non |
| 27 | 250 | 0 | 100 | non |
| 29 | 250 | 0 | 100 | non |

EXPERIMENT 8

Test for Control on Damping-Off Disease of Cucumber Seedling

A Neubauer pot was filled with field soil, and pathogenic soil in which *Pythium aphanidernatum* had been cultivated was blended with the field soil in a layer of a depth of 2 cm in the pot to inoculate the soil with the pathogenic fungus. The pot was allowed to stand at 28° C. under super humid conditions for 24 hours in a greenhouse, and subjected to soil injection treatment at a predetermined dose level with wettable powder of Formulation 2 described below which had been diluted with water. Ten seeds of cucumber (Ociai-aonagafushinari strain) were sown and lightly covered with the same field soil. After two week cultivation under greenhouse conditions, the seedlings were checked for the occurrence of infection, and the good seedling rate was calculated by the following equation:

$$\text{Good seedling rate (\%)} = \frac{\text{number of good seedlings in test section}}{\text{number of seedlings germinating}} \times 100.$$

in untreated and non-inoculated section

The results are shown in Table 9 below.

TABLE 9

| Compound No. | Concentration of the compound (mg/pot) | Good seadling rate (%) |
| --- | --- | --- |
| untreated section | — | 0 |
| 4 | 20 | 100 |
| 8 | 20 | 100 |
| 11 | 20 | 100 |
| 16 | 20 | 100 |
| 18 | 20 | 100 |
| 22 | 20 | 100 |
| 26 | 20 | 100 |
| 27 | 20 | 100 |
| 28 | 20 | 100 |
| 29 | 20 | 100 |
| 34 | 20 | 100 |

This invention is further illustrated by the following Formulation Examples. It should be understood that the active compounds, carriers, adjuvants and the mixing proportions of the formulation of this invention are not limited to the following Formulations. Incidentally, all parts in the Formulation Examples are by weight.

FORMULATION 1: DUST

Compound No. 11: 2 parts
Clay: 98 parts

The components above were thoroughly mixed and finely divided to give dust.

FORMULATION 2: WETTABLE POWDER

Compound No. 4: 10 parts
Sodium alkylsulfonate: 5 parts
Clay: 85 parts

All the components above were thoroughly mixed and finely divided to give wettable powder.

FORMULATION 3: EMULSIFIABLE CONCENTRATE

Compound No. 27: 5 parts
Calcium alkylbenzenesulfonate: 4 parts
Polyoxyethylene alkylphenyl ether: 11 parts
Cyclohexanone: 10 parts
Xylene: 70 parts All the components were mixed uniformly to give an emulsifiable concentrate. For use, this emulsifiable concentrate is diluted with water to a desired level and sprayed.

FORMULATION 4: EMULSIFIABLE CONCENTRATE

Compound No. 29: 10 parts
Calcium alkylbenzene sulfonate: 3 parts
Polyoxyethylene alkylphenyl ether: 12 parts
Dimethylformamide: 10 parts
Xylene: 65 parts All the components were mixed uniformly to give an emulsifiable concentrate.

FORMULATION 5: GRANULES

Compound No. 22: 2 parts
Calcium lignin sulfonate: 2 parts
Bentonite: 30 parts
Talc: 66 parts All the components were mixed uniformly. Water was added to the mixture and kneaded, granulated, and dried to give granules.

FORMULATION 6: SUSPENSION CONCENTRATE

Compound No. 8: 10 parts
Ethylene glycol: 5 parts
Xanthan gum: 0.2 parts
Polyoxyethylene sorbitan mono-oleate: 5 parts
Water: 79.8 parts All the components were mixed and wet-pluverized to give a suspension concentrate.

What is claimed is:

1. A 4H-3,1-benzoxazine derivative of the formula (I):

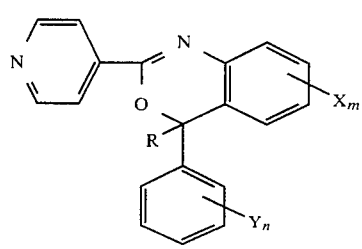

wherein X and Y each independently represent a halogen atom or a lower alkyl group having 1-4 carbons; m and n each independently represent an integer of 0 to 2, and when m or n is 2, the plurality of each of X or Y may have the same or different meanings; R is a hydrogen atom, an alkyloxy group having 1-5 carbons, an alkynyloxy group having up to 5 carbons, an alkylthio group having 1-5 carbons or an alkenylthio group having up to 5 carbons.

2. A compound according to claim 1 wherein X is a halogen atom and m is 1-2.

3. A compound according to claim 1 wherein X is a lower alkyl group and n is 1-2.

4. A compound according to claim 1 wherein Y is a hydrogen atom.

5. A compound according to claim 1 wherein Y is a lower alkyl group.

6. A compound according to claim 1 wherein R is a hydrogen atom.

7. A compound according to claim 1 wherein R is an alkyloxy group having 1-4 carbons.

8. A compound according to claim 1 wherein R is an alkynyloxy group having 2-3 carbons.

9. A compound according to claim 1 wherein R is an alkylthio group having 1-3 carbons.

10. A compound according to claim 1 wherein R is an alkenylthio group having 2-3 carbons.

11. An agricultural or horticultural composition comprising a fungicidally effective amount of at least one 4H-3,1-benzoxazine derivative of the formula (I):

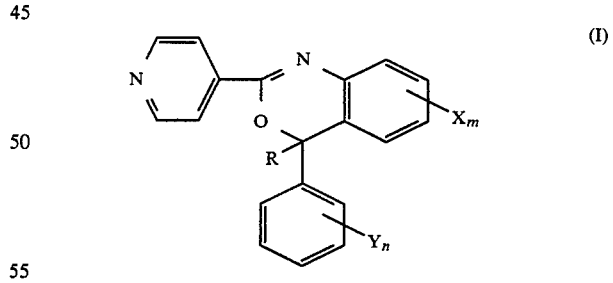

wherein X and Y each independently represent a halogen atom or a lower alkyl group of 1-4 carbons; m and n each independently represent an integer of 0 to 2, and when m or n is 2, the plurality of each of X or Y may have the same or different meanings; R is a hydrogen atom, and alkyloxy group of 1-5 carbons, an alkynyloxy group of up to 5 carbons, an alkylthio group of 1-5 carbons or an alkenylthio group of up to 5 carbons; and an agriculturally or horticulturally acceptable carrier.

12. A composition according to claim 11 in the form of a wettable powder, an emulsifiable concentration, an oil, a dust, a granule or a suspension concentrate.

13. A method of controlling pathogenic fungi on plants or in soil by applying a 4H-3,1-benzoxazine derivative of the following formula (I):

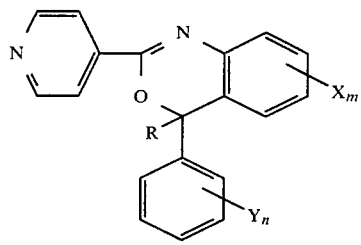
(I)

wherein X and y each independently represent a halogen atom or a lower alkyl group of 1-4 carbons; m and n each independently represent an integer of 0 to 2, and when m or n is 2, the plurality of each of X or Y may have the same or different meanings; and R is a hydrogen atom, an alkyloxy group of 1-5 carbons, an alkynyloxy group of up to 5 carbons, an alkylthio group of 1-5 carbons or an alkenylthio group of up to 5 carbons, to the plant or the locus thereof.

14. A method according to claim 13 wherein said compound is used in an amount of 0.5 to 500 g for 10 ares.

15. A method according to claim 13 wherein said compound is used in an amount of 1 to 250 g for 10 ares.

16. An agricultural or horticultural fungicide composition comprising a 4H-3,1-benzoxazine derivative of the formula (I):

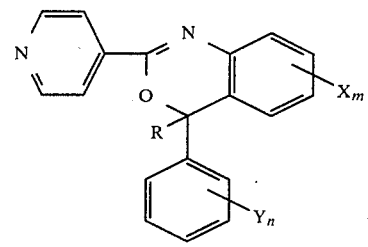
(I)

wherein X and Y each independently represent a halogen atom or a lower alkyl group of 1-2 carbons; m and n each independently represent an integer of 0 to 2, and when m or n is 2, the plurality of each of X or Y may have the same or different meanings; and R is a hydrogen atom, an alkyloxy group of 1-4 carbons, propargyloxy, an alkylthio group of 1-3 carbons or allylthio, together with a solid or liquid carrier and a optional adjuvant.

17. A composition according to claim 16 which comprises 0.05 to 95% by weight of said compound, together with 70 to 99% by weight of the carrier and 0 to 20% by weight of the adjuvant.

18. A composition according to claim 16 which comprises 0.1 to 80% by weight of said compound, together with 70 to 99% by weight of the carrier and 0 to 20% by weight of the adjuvant.

19. A composition according to claim 16 which comprises 1 to 70% by weight of said compound, together with 70 to 99% by weight of the carrier and 0 to 20% by weight of the adjuvant.

* * * * *